United States Patent

Uemura et al.

[11] Patent Number: 6,080,373
[45] Date of Patent: Jun. 27, 2000

[54] METHOD OF CONTACTING CATALYST PARTICLES WITH GAS AND LIQUID

[75] Inventors: Fumihiko Uemura, Kawasaki; Hideki Sugiyama, Yokohama; Chieko Nagasawa, Kamakura; Takeshi Minami, Yokohama; Kazuhiko Hamato, Kawasaki; Noriyuki Yoneda, Tokyo; Akihisa Yamaguchi, Yokohama, all of Japan

[73] Assignee: Chiyoda Corporation, Japan

[21] Appl. No.: 08/939,622

[22] Filed: Sep. 29, 1997

Related U.S. Application Data

[62] Division of application No. 08/413,626, Mar. 30, 1995, Pat. No. 5,880,311.

[30] Foreign Application Priority Data

Jul. 22, 1994 [JP] Japan .................................. 6-191955
Dec. 29, 1994 [JP] Japan .................................. 6-340241
Dec. 29, 1994 [JP] Japan .................................. 6-340242

[51] Int. Cl.$^7$ ........................................................ B01J 8/22
[52] U.S. Cl. ........................... 422/211; 422/212; 422/213; 422/230; 422/234; 422/235
[58] Field of Search ...................................... 422/211, 234, 422/235, 212, 213, 230

[56] References Cited

U.S. PATENT DOCUMENTS

| | | | |
|---|---|---|---|
| 3,864,236 | 2/1975 | Lindstrom | 204/265 |
| 4,203,927 | 5/1980 | Stapp | 568/401 |
| 5,009,851 | 4/1991 | Avidan et al. | 422/141 |

*Primary Examiner*—Hien Tran
*Assistant Examiner*—Frederick Varcoe
*Attorney, Agent, or Firm*—Lorusso & Loud

[57] ABSTRACT

Catalyst particles are contacted with a liquid and a gas in a vertically extending cylindrical vessel. The particles and liquid are placed in the vessel into which the gas and liquid are continuously fed from the bottom thereof so that an upwardly flowing mixture comprising the particles, liquid and gas is formed. The mixture is introduced into a gas separating zone disposed adjacent to an upper portion of the vessel to separate the mixture by gravity into a gas phase, a supernatant liquid phase and a phase rich in the catalyst particles. The gas and supernatant phases are continuously withdrawn from the separating zone while the catalyst particles-rich phase is continuously recycled to the bottom of the vessel by gravity.

13 Claims, 6 Drawing Sheets

METHOD OF CONTACTING CATALYST PARTICLES WITH GAS AND LIQUID

This application is a division of application Ser. No. 08/413,626 filed Mar. 30, 1995 which application is now issued as U.S. Pat. No. 5,880,311.

BACKGROUND OF THE INVENTION

This invention relates generally to a method of contacting catalyst particles with a liquid and a gas and, more specifically, to a liquid phase reaction method using a particulate catalyst. The present invention is also directed to a device useful for carrying out the above method.

In order to uniformly mix catalyst particles with a gas and a liquid and to effectively carry out a catalytic reaction, it has been a general practice to use a stirrer. In this case, however, the catalyst particles are gradually physically pulverized as the reaction is continued for a long period of time, especially when the catalyst particles have low mechanical strengths and are fragile. The pulverized particles are entrained by the product stream discharged from the reactor to cause a change in the concentration of the catalyst in the reactor and to contaminate the product.

For example, U.S. Pat. No. 5,155,261 discloses a process for producing acetic acid by reacting methanol in a solvent with carbon monoxide in the presence of an alkyl iodide and a solid catalyst containing a rhodium complex supported on a porous, cross-linked vinyl pyridine resin carrier. Because the vinyl pyridine resin is gradually abraded or pulverized as the carbonylation is continued, the pulverization of the catalyst not only causes the reduction of the catalyst life but also requires the separation of the pulverized powder from the reaction product. Since the rhodium-supported catalyst is very expensive, the pulverization of the catalyst poses a serious problem.

SUMMARY OF THE INVENTION

It is, therefore, the prime object of the present invention to provide a method which permits effective contact of catalyst particles with a gas and a liquid without causing pulverization of the particles.

Another object of the present invention is to provide a device useful for performing the above method.

It is a special object of the present invention to provide a method and a device by which carbonylation of methanol using a rhodium-supported catalyst can be continuously performed in a stable manner for a long period of time.

In accomplishing the foregoing objects, there is provided in accordance with one aspect of the present invention a method of contacting catalyst particles with a gas and a liquid having a specific gravity smaller than that of said catalyst particles, said method comprising the steps of:

(a) placing said catalyst particles in a vertically extending cylindrical vessel having upper and lower portions;

(b) continuously feeding said liquid to said vessel from said lower portion to fill said vessel therewith;

(c) continuously feeding said gas to said vessel from said lower portion and bubbling said gas through said liquid to form an upwardly flowing mixture comprising said particles, said liquid and said gas;

(d) continuously introducing said upwardly flowing mixture into a gas separating zone disposed adjacent to said upper portion of said vessel to separate said mixture by gravity into a gas phase, a supernatant liquid phase and a phase rich in said catalyst particles;

(e) continuously withdrawing said gas phase from said separating zone;

(f) continuously discharging said supernatant liquid phase from said separating zone;

(g) continuously discharging said catalyst particles-rich phase from said separating zone; and (h) continuously recycling said discharged catalyst particles-rich phase to said lower portion of said vessel by gravity.

In another aspect, the present invention provides a carbonylation method wherein a carbonylatable compound in a liquid phase is reacted with carbon monoxide in the presence of a metal carbonyl iodide complex catalyst and an alkyl iodide, characterized in that said reaction is performed in a reactor whose inside surface is formed of titanium, in that said reaction is carried out while keeping the content of water in said liquid phase no more than 10% by weight, and in that that portion of said reactor above the liquid level of said liquid phase is continuously washed with a cleaning liquid containing less than 3,000 ppm by weight of hydrogen iodide.

The present invention also provides a carbonylation method wherein a carbonylatable compound in a liquid phase is reacted, in a reactor, with carbon monoxide in the presence of a metal carbonyl iodide complex catalyst and an alkyl iodide, characterized in that that portion of the inside surface of said reactor which is in contact with said liquid phase is formed of titanium, in that that portion of the inside surface of said reactor that is located above the liquid level of said liquid phase is formed of a titanium-palladium alloy, and in that said reaction is carried out while keeping the content of water in said liquid phase no more than 10% by weight.

In a further aspect, the present invention provides a device for contacting catalyst particles with a gas, a liquid having a specific gravity smaller than that of said catalyst particles, said device comprising:

(a) a vertically extending cylindrical vessel for containing said liquid and said catalyst particles, said vessel having upper and lower portions;

(b) a liquid feed conduit connected to said lower portion for feeding said liquid to said vessel;

(c) gas injection means provided in said lower portion for injecting said gas into said vessel and for bubbling said gas through said liquid such that an upwardly flowing mixture comprising said liquid, said particles and said gas is formed within said vessel;

(d) a gas separating chamber disposed adjacent to said upper portion of said vessel for receiving said upwardly flowing mixture and separating same by gravity into a gas phase, a supernatant liquid phase and a phase rich in said catalyst particles;

(e) a gas discharge conduit connected to an top portion of said separating chamber for withdrawing said gas phase from said separating chamber;

(f) a liquid discharge conduit connected to an upper portion of said separating chamber for discharging a portion of said supernatant liquid phase from said separating chamber; and (g) a recycling path extending between said separating chamber and said lower portion of said vessel for recycling said catalyst particles-rich phase from said separating chamber to said vessel by gravity.

The present invention further provides a device for contacting catalyst particles with a gas and a liquid having a specific gravity smaller than that of said catalyst particles, said device comprising:

(a) a vertically extending cylindrical vessel for containing said liquid and said catalyst particles, said vessel having upper and lower portions;

(b) a liquid feed conduit connected to said lower portion for feeding said liquid to said vessel therethrough;

(c) gas injection means provided in said lower portion for injecting said gas into said vessel and for bubbling said gas through said liquid such that an upwardly flowing mixture is formed within said vessel;

(d) a first separating chamber connected to said upper portion of said vessel for receiving said upwardly flowing mixture and separating same by gravity into a first gas phase, a first supernatant liquid phase and a first catalyst particles-rich phase;

(e) a gas discharge conduit connected to a top portion of said separating chamber for withdrawing said first gas phase from said separating chamber;

(f) a second separating chamber connected to said upper portion of said vessel, so that a portion said upwardly flowing mixture and said first catalyst particles-rich phase are introduced into said second separating chamber and are separated into a second gas phase, a second supernatant liquid phase and a second catalyst particle-rich phase;

(g) a gas withdrawing conduit connected to a top portion of said second separating chamber for discharging said second gas phase from said second separating chamber;

(h) a liquid discharge conduit connected to an upper portion of one of said first and second separating chambers for discharging a portion of said first or second supernatant liquid phase from said first or second separating chambers; and (i) a recycling path extending between said degassing chamber and said lower portion of said vessel for recycling said catalyst particle-containing liquid from said degassing chamber to said vessel by gravity.

BRIEF DESCRIPTION OF THE DRAWINGS

Other objects, features and advantages of the present invention will become more apparent from the detailed description of the preferred embodiments of the invention which follows, when considered in light of the accompanying drawings, in which.

Detailed Description of the Preferred Embodiments of the Invention

Figure 1:
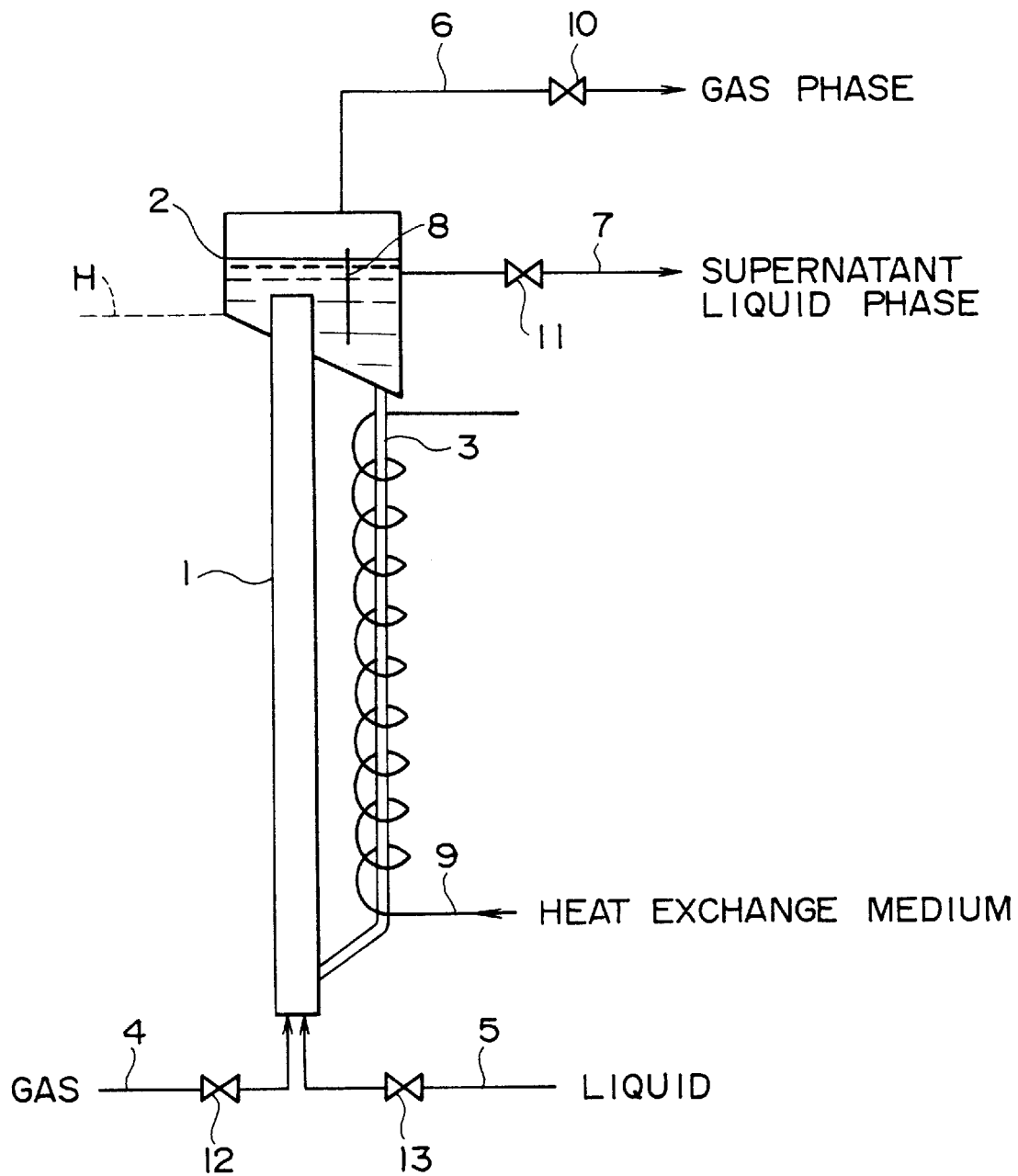
FIGS. 1–6 are each an elevational view diagrammatically showing a device for contacting catalyst particles with a liquid and a gas according to the present invention.

Referring now to FIG. 1, a device for contacting catalyst particles with a gas and a liquid according to the present invention includes a vertically extending cylindrical vessel 1 adapted for containing the liquid and the catalyst particles. A liquid feed conduit 5 is connected to a lower portion of the vessel 1 for feeding the liquid to the vessel therethrough. Also connected to the lower portion of the vessel 1 is a gas feeding conduit 4 for feeding the gas into the vessel 1 therethrough. A gas injection nozzle (not shown) is connected to the conduit 4 so that the gas is injected from the nozzle and is bubbled through the liquid contained in the vessel 1. As a consequence of the gas injection, there is formed an upwardly flowing mixture including the liquid, the particles and the gas within the vessel 1.

Designated as 2 is a gas separating chamber disposed to surround an upper portion of the vessel 1 for receiving the upwardly flowing mixture from the vessel 1. In the chamber 2, the mixture is separated by gravity into a gas phase, a supernatant liquid phase and a phase rich in the catalyst particles. In order to facilitate the separation in the chamber 2, it is preferred that the horizontal sectional area of the chamber 2 be 2–200 times, more preferably 5–100 times, as large as that of the vessel 1.

A gas discharge conduit 6 is connected to a top portion of the separating chamber 2 for withdrawing the gas phase from the separating chamber 2 therethrough. A liquid discharge conduit 7 is connected to an upper portion of the separating chamber 2 for discharging a portion of the supernatant liquid phase from the separating chamber 2 therethrough. The conduit 7 is preferably positioned slightly below the liquid level in the chamber 2. Designated as 8 is a flow control plate suitably disposed to prevent the gas from discharging through the conduit 7 together with the supernatant liquid phase. The top end of the vessel 1 is preferably located below the liquid level (as shown in FIG. 1) but may be above the liquid level as long as the gas and particles are prevented from entering the supernatant liquid phase discharging conduit 7.

A recycling pipe 3 extends between the separating chamber 2 and the lower portion of the vessel 1 so that the catalyst particles-rich phase collected in the bottom of the chamber 2 is recycled from the separating chamber 2 to the vessel 1 by gravity through the pipe 3. Namely, since the specific gravity of the catalyst particles is greater than that of the liquid and since the apparent specific gravity of the mixture in the vessel 1 which contains the gas is smaller than the solid-rich phase in the chamber 2 which does not contain the gas, there is established a recirculating stream of the ascending flow in the vessel 1 and a descending flow in the recycling pipe 3 by injecting the gas into the vessel 1 containing the liquid and the catalyst particles. During the upward movement of the mixture through the vessel 1, the catalyst particles are effectively contacted with the gas and the liquid.

If desired, a temperature controlling device 9 such as a heat exchanger may be disposed in the recycling pipe 3 to heat or cool the catalyst particles-rich phase flowing through the pipe 3 and to maintain the temperature of the mixture in the vessel 1 at a desired temperature. Reference numerals 10–13 designate flow control valves.

Figure 2:
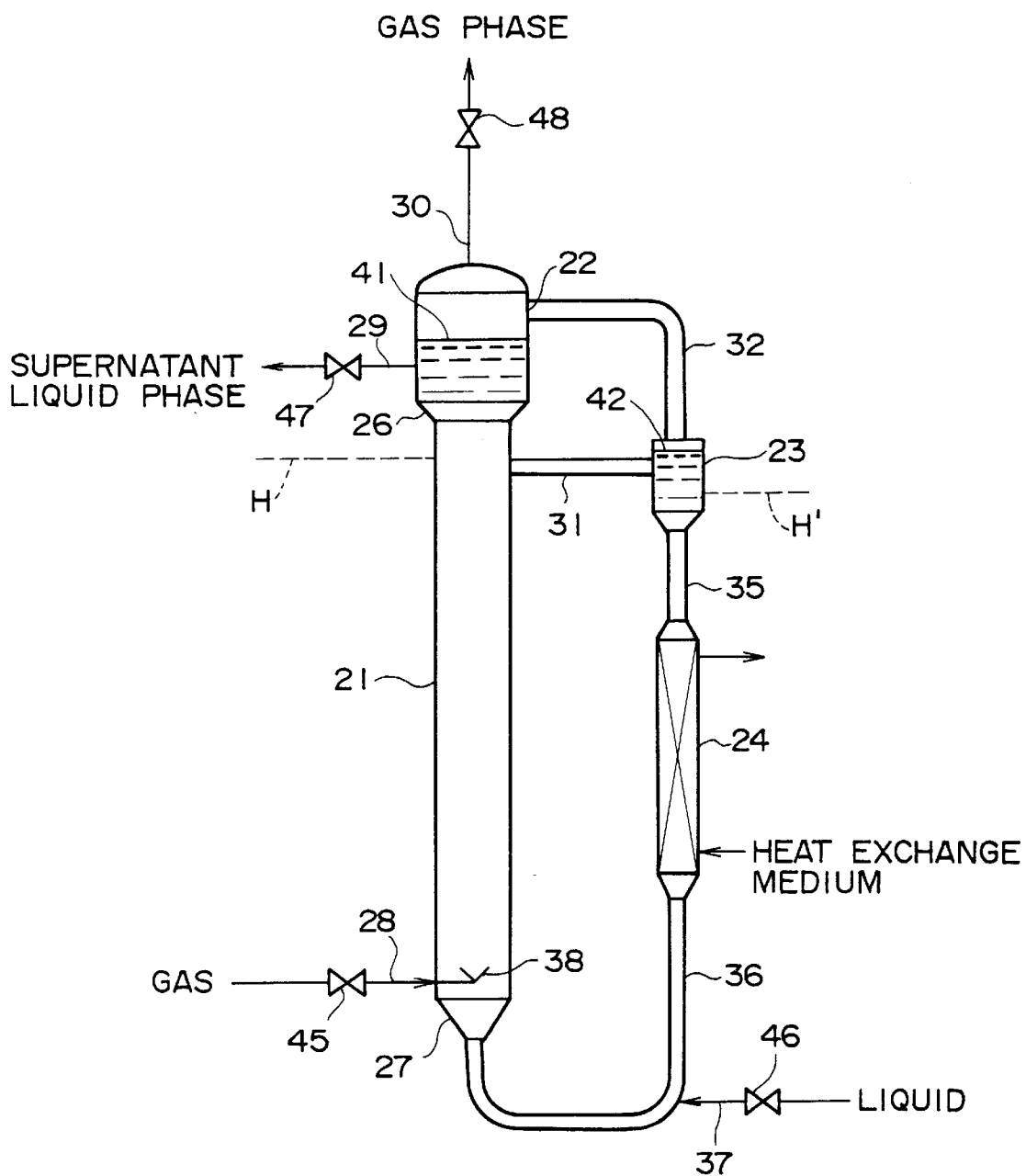

FIG. 2 depicts another embodiment of a device for contacting catalyst particles with a gas and a liquid according to the present invention. The device includes a vertically extending cylindrical vessel 21 adapted for containing the liquid and the catalyst particles. The height of the vessel 21 is preferably 5–100 times, more preferably 10–20 times, that of the inside diameter thereof. A liquid feed conduit 37 is connected to a lower portion 27 of the vessel 21 for feeding the liquid to the vessel 21 therethrough. Also connected to the lower portion of the vessel 21 is a gas feeding conduit 28 for feeding the gas into the vessel 21 therethrough. A gas injection nozzle 38 is connected to the conduit 28 so that the gas is injected from the nozzle 38 and is bubbled through the liquid contained in the vessel 21. As a consequence of the gas injection, there is formed an upwardly flowing mixture including the liquid, the particles and the gas within the vessel 21. The nozzle 38 may have only one gas injection hole but preferably has a plurality of gas injection holes for forming fine gas bubbles. The force by which the catalyst particles are upwardly moved through the vessel 21 depends upon the linear velocity of the liquid upwardly flowing therethrough. Thus, by controlling the linear velocity of the liquid in the vessel 21 at a level higher than that at which the catalyst particles fall by gravity in the liquid, it is possible to upwardly move the catalyst particles through the vessel 21. The linear velocity of the liquid may be controlled by the rate of the gas feed through the conduit 28.

Designated as 22 is a first separating chamber connected to an upper end of the vessel 21 through an upwardly enlarged section 26 for receiving the upwardly flowing mixture from the vessel 21. The chamber 22 has a horizontal sectional area which is 1–10 times, preferably 2–5 times, as large as that of the vessel 21. In the chamber 22, the mixture is separated by gravity into a first gas phase, a supernatant liquid phase and a phase rich in the catalyst particles. Since the horizontal sectional area of the chamber 22 is larger than that of the vessel 21, the linear velocity of the liquid is reduced upon entering the chamber 22 so that the catalyst particles contained therein precipitate to form the catalyst particles-rich phase in a region including the bottom of the chamber 22 and an upper portion of the vessel 21.

A gas discharge conduit 30 is connected to a top portion of the separating chamber 22 for withdrawing the first gas phase from the separating chamber 22 therethrough. A liquid discharge conduit 29 is connected to an upper portion of the separating chamber 22 for discharging a portion of the supernatant liquid phase from the separating chamber 22 therethrough.

Designated as 23 is a second separating chamber. The second chamber 23 is connected to an upper portion of the vessel 21 through a connecting pipe 31, so that a portion the catalyst particles-rich phase which has been separated in the first separating chamber 22 is introduced, together with a portion of the mixture upwardly flowing through the vessel 21, into the second chamber 23 through the pipe 31 and is separated into a second gas phase and a catalyst particle-containing liquid. The second chamber 23 has a horizontal sectional area which is 1–10 times, preferably 2–5 times, as large as that of the vessel 21. The connecting pipe 31 is generally oriented horizontally or downwarly toward the second chamber 23

A gas withdrawing conduit 32 extends between a top portion of the second chamber 23 and an upper portion of the first chamber 22 above the liquid level 41 thereof, so that the second gas phase above the liquid level 42 in the second chamber 23 is discharged from the second chamber 23, introduced into the upper space above the liquid level 41 in the first chamber 22 and withdrawn from the first chamber 22 together with the first gas phase.

A recycling path including pipes 35 and 36 extends between the second chamber 23 and a lower portion of the vessel 21 for recycling the catalyst particle-containing liquid from the second chamber 23 to the vessel 21 by gravity. Because the gas separation is carried out in both first and second chambers 22 and 23, the content of the gas in the catalyst particle-containing liquid formed in the second chamber 23 is much smaller than the catalyst particles-rich phase formed in the chamber 2 of above embodiment shown in FIG. 1, so that the difference in specific gravity between the mass in the vessel 21 and the mass in the recycling path defined by pipes 35 and 36 is greater than that between the vessel 1 and the recycling pipe 3. Therefore, the embodiment shown in FIG. 2 provides more efficient recycling and more effective contact of the catalyst particles with the gas and liquid as compared with the embodiment of FIG. 1.

Designated as 24 is a heat exchanger optionally disposed in the recycling path defined by pipes 35 and 36 to heat or cool, with the heat exchanger medium, the catalyst particle-containing liquid flowing through the recycling path and to maintain the temperature of the mixture in the vessel 21 at a desired temperature. Reference numerals 45–48 designate flow control valves.

Figure 3:
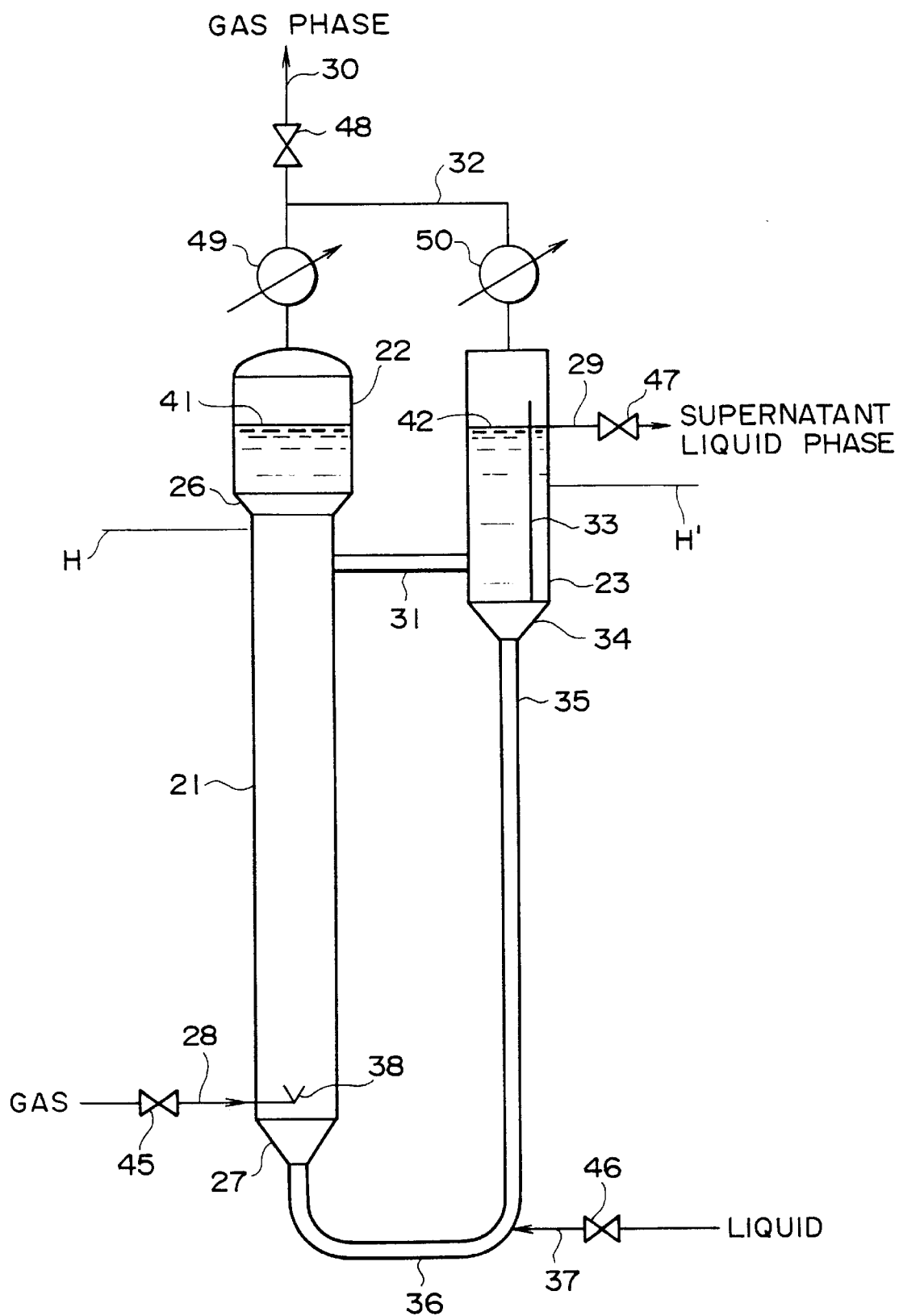

FIG. 3 shows a modified embodiment of the device of FIG. 2, in which the reference numerals similar to those in FIG. 2 designate the same component parts. In this embodiment, the second separating chamber 23 is vertically extended with the inside diameter being preferably 0.5–5 times, more preferably 1–3 times, that of the vessel 21. The supernatant liquid phase discharging conduit 29 is connected to a bottom portion 34 of the second separating chamber 23. Designated as 33 is a flow control plate suitably disposed to prevent the gas from discharging through the conduit 29 together with the supernatant liquid phase. Designated as 49 and 50 are condensers to condense part of respective gas phases, with the condensed liquid being returned to respective separating chambers 22 and 23.

Figure 4:
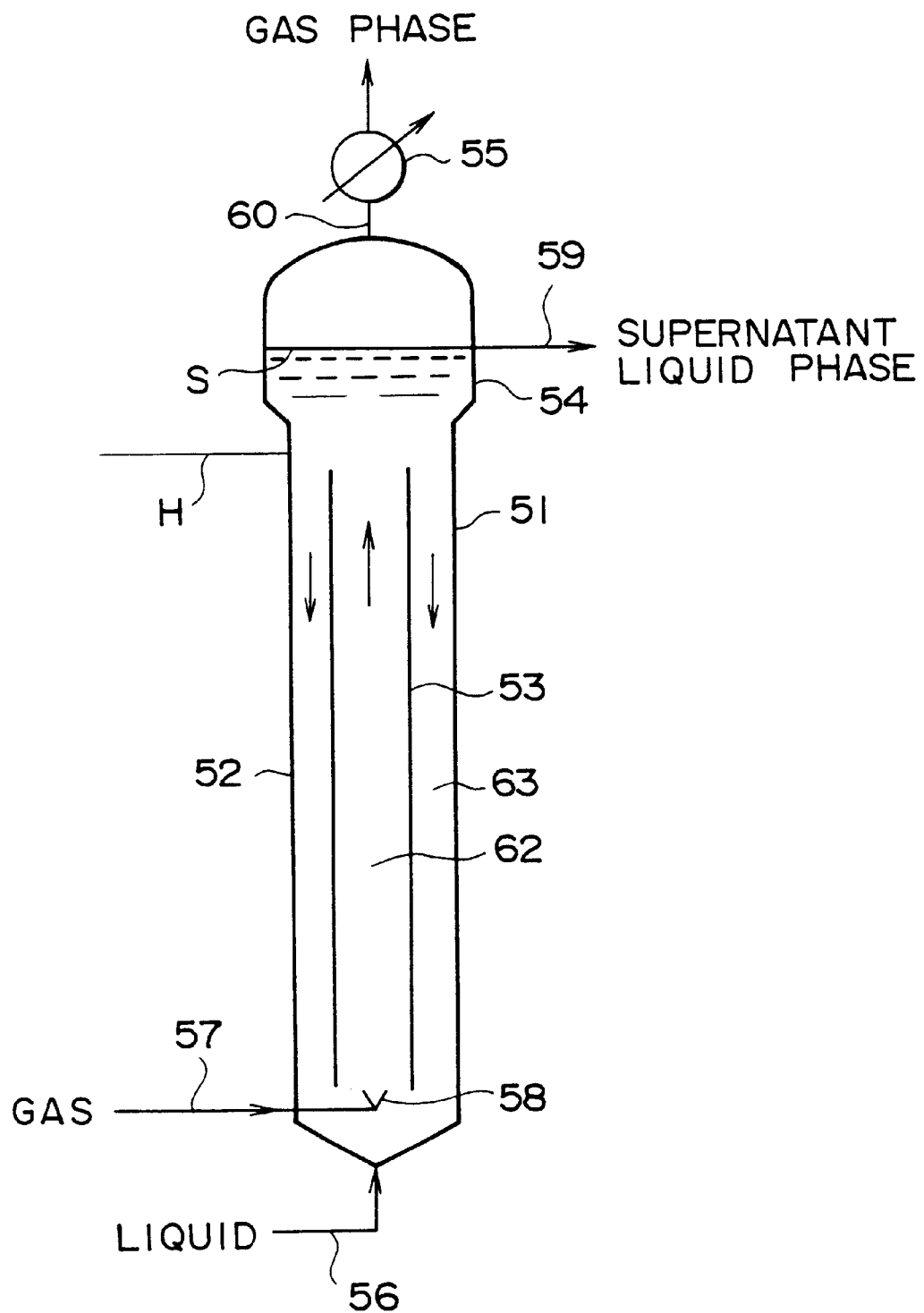

FIG. 4 depicts a further embodiment of a device for contacting catalyst particles with a gas and a liquid according to the present invention. The device, generally denoted by the reference numeral 51, includes an outer vertically extending cylindrical housing 52 and an inner vertically extending cylindrical pipe 53 which defines a contacting zone 62 therein and which is coaxial placed inside of the housing 52 to define an annular recycling path 63 between them. Similar to the foregoing embodiments, a liquid feed conduit 56 and a gas feeding conduit 57 are connected to a lower portion of the housing 52. A gas injection nozzle 58 is connected to the conduit 57. Disposed above the housing 52 is a separating chamber 54 having a horizontal sectional area greater than that of the housing 52. A gas discharge conduit 60 having a condenser 55 is connected to a top portion of the separating chamber 54 and a liquid discharge conduit 59 is connected to an upper portion of the separating chamber 54.

The device 51 operates as follows. After placing the catalyst particles in the housing 52, the liquid is fed from the conduit 56 to fill the housing 52 up to a level "H". The gas is then injected from the nozzle 58 so that the liquid level is raised to the position "S". The feed of the gas is continued while feeding the liquid from the conduit 56. Thus, there is formed an upwardly flowing stream of a mixture of the gas, liquid and catalyst particles in the contacting zone 62. The mixture is separated in a gas phase which is withdrawn overhead through the line 60, a supernatant liquid phase which is discharged through the line 59 and a catalyst particles-rich phase which is recycled through the recycling path 63 to the bottom of the contacting zone 62.

The contacting device according to the present invention may be used for carrying out a variety of liquid phase catalytic reactions such as (a) a reaction between two or more gaseous reactants, (b) a reaction between two or more liquid reactants and (c) a reaction between one or more gaseous reactant with one or more liquid reactants. In the case of (a), the liquid serves as a solvent, while, in the case of (b), the inert gas serves only to circulate the catalyst particles. Illustrative of the catalytic reactions suitably performed with the device according to the present invention are (1) hydrodesulfurization of hydrocarbon oils using composite catalyst containing nickel, molybdenum, cobalt and/or platinum, (2) hydrogenation of fatty oils, unsaturated hydrocarbons, unsaturated fatty acids or unsaturated fatty esters using a hydrogenation catalyst, (3) hydrogenative reduction of esters to alcohols using a hydrogenation catalyst, (4) carbonylation of methanol in an acetic acid solvent with carbon monoxide using a rhodium complex resin carried on a pyridine resin, and (5) conversion of an olefin in a solvent into an aldehyde or an ester by reaction with carbon monoxide and hydrogen using a catalyst containing a carbonyl complex of a transition element such as cobalt or rhodium.

Above all, the contacting device of the present invention is advantageously used for the carbonylation of compound in the presence of a catalyst which comprises a rhodium complex supported on a porous, cross-linked vinylpyridine resin. The carbonylation of a carbonylatable compound will be described in detail below.

Carbonylatable Compound:

Alcohols, ethers and esters may be used as the raw material for the carbonylation. These compounds may be aromatic, aliphatic or heterocyclic compounds. Illustrative of suitable carbonylatable alcohols are benzyl alcohol, furfuryl alcohol and aliphatic alcohols having 1–6 carbon atoms, such as methanol, ethanol, propanol and butanol. Illustrative of suitable carbonylatable ethers are aliphatic ethers having 2–12 carbon atoms such as dimethyl ether, diethyl ether, dipropyl ether and methyl ethyl ether. Illustrative of suitable esters are those of aliphatic carboxylic acids having 1–6 carbon atoms with aliphatic alcohols having 1–6 carbon atoms, such as methyl acetate, ethyl acetate, propyl acetate, butyl acetate, amyl acetate, hexyl acetate, methyl propionate, ethyl propionate, propyl propionate, butyl propionate, hexyl propionate, methyl butyrate, ethyl butyrate, propyl butyrate, butyl butyrate, amyl butyrate, hexyl butyrate, methyl valerate, ethyl valerate, propyl valerate, methyl caproate, ethyl caproate and propyl caproate.

An alcohol, an ether and an ester are carbonylated as follows ($R^1$ and $R^2$ each represent a hydrocarbyl group):

(1) Alcohol carbonylation:

$$R^1OH + CO \rightarrow R^1COOH$$

(2) Ether carbonylation:

$$R^1OR^2 + H_2O \rightarrow R^1OH + R^2OH$$

$$R^1OH + CO \rightarrow R^1COOH$$

$$R^2OH + CO \rightarrow R^2COOH$$

(3) Ester carbonylation:

$$R^1COOR^2 + H_2O \rightarrow R^1COOH + R^2OH$$

$$R^2OH + CO \rightarrow R^2COOH$$

Carbonylation Catalyst:

It is preferred that the vinylpyridine resin have a cross-linking degree of 30–60%, preferably 35–60%, a pore volume of 0.2–0.4 cc/g, preferably 0.25–0.4 cc/g, and an average pore diameter of 20–100 nm, preferably 30–90 nm. This catalyst has an improved catalyst life and exhibits good mechanical strengths (e.g. resistance to abrasion and crushing) and high catalytic activity.

The term "cross-linking degree" herein is defined as follows:

$$\text{Cross-linking degree (\%)} = (A/B) \times 100$$

wherein A represents the weight of the cross-linking agent contained in the VP resin and B represents the weight of the vinylpyridine monomer units of the VP resin.

The "pore volume" of the VP resin is measured by the mercury penetration method using Mercury Pressure Porosimeter Model 70 (manufactured by Carlo Elba Inc., Italy) with a mercury surface tension of 474 dyne/cm at 25 C, a contact angle of 140 degrees and an absolute mercury pressure varying from 1 to 200 kg/cm$^2$.

The term "average pore diameter" used herein is defined as follows:

$$\text{Average pore volume (nm)} = 4(C/D) \times 10^3$$

wherein C represents the pore volume (cc/g) of the VP resin and D represents the surface area (m$^2$/g) of the VP resin measured by the B. E. T. method.

The VP resin may be produced by copolymerizing a vinylpyridine monomer with an aromatic compound having two vinyl groups as a cross-linking agent. The copolymerization method is well known in the art and may be, for example, a method in which a precipitant is added, a method in which a linear polymer is added, a method in which a swelling agent and a precipitant are added, and a method in which a diluent and a linear polymer are added. The method disclosed in Japanese Published Examined Patent Application No. 61-25731 may be particularly suitably used. In this method, a mixture containing a vinyl pyridine monomer, a cross-linking agent having two vinyl groups and, optionally, a vinyl monomer is reacted in the presence of a radical polymerization catalyst, a suspension stabilizing agent and a precipitant using an aqueous suspension polymerization technique. The stabilizer may be a water-soluble polymer such as polyvinyl alcohol, hydroxyethyl cellulose, carboxymethyl cellulose, sodium polymethacrylate, sodium polyacrylate, starch, gelatin, or an ammonium salt of styrene/meleic anhydride copolymer, or an inorganic salt such as calcium carbonate, calcium sulfate, bentonite or magnesium silicate. The precipitant is an organic liquid which serves to function as a good solvent for the monomer but as a poor solvent for the copolymer produced. Examples of the precipitant includes hydrocarbons having 5–10 carbon atoms such as isooctane, alcohols and esters. The polymerization degree of the VP resin may be controlled by control of the amount of the cross-linking agent. The pore volume and the average pore diameter may be controlled by selection of the kind and amount of the precipitant. Suitable selection of the kind and amount of the suspension stabilizer and the reaction temperature is also effective to control the pore characteristics of the VP resin.

Illustrative of suitable vinylpyridine monomers for the production of the VP resin are 4-vinylpyridine, 2-vinylpyridine and 2- and 4-vinylpyridine derivatives having a lower alkyl group such as a methyl group or ethyl group on the pyridine ring. The vinylpyridine monomer may be used in conjunction with an aromatic vinyl monomer such as styrene or vinyltoluene. Such a vinyl monomer is used in an amount of 30 mole % or less, preferably 20 mole % or less based on the total mole of total monomers. Illustrative of suitable cross-linking agents are aromatic divinyl compounds such as divinylbenzene and divinyltoluene and aliphatic divinyl compounds such as butadiene. The amount of the cross-linking agent is determined according to the intended cross-linking degree.

The VP resin is generally used in the form of beads, preferably spheres, having a particle size of 0.01–4 mm, preferably 0.1–2 mm, more preferably 0.4–2 mm. The VP resin is loaded with a rhodium complex $[Rh(CO)_2I_2]^-$ in any suitable manner. The amount of the rhodium complex loaded on the VP resin is 0.2–2% by weight, preferably 0.5–1.0% by weight, in terms of elemental rhodium, based on the weight of the VP resin.

The loading of the VP resin with the rhodium complex may be performed by contacting the VP resin with a rhodium salt in a solvent containing an alkyl iodide under a pressure of carbon monoxide. This method may be carried out by contacting the rhodium salt with the VP resin under conditions as generally adopted in the catalytic carbonylation of methanol. During the course of the above reaction, the pyridine ring of the VP resin are quaternized with the alkyl iodide to form a pyridinium salt to which is ionically bonded a rhodium carbonyl complex $[Rh(CO)_2I_2]^-$ formed by reaction of the rhodium salt, alkyl iodide and carbon monoxide.

Examples of the rhodium salts include rhodium halides such as rhodium chloride, rhodium bromide and rhodium iodide. Illustrative of suitable alkyl iodides are lower alkyl iodides such as methyl iodide, ethyl iodide and propyl iodide. The use of methyl iodide is preferred. The alkyl iodide is used in an amount of 2–2,000 moles, preferably 5–500 moles, per mole of the rhodium salt. The carbon monoxide pressure under which the rhodium salt is contacted with the VP resin in the presence of the alkyl iodide is 7–30 kg/cm$^2$G, preferably 10–20 kg/cm$^2$G.

The loading of the VP resin with the rhodium complex may be also performed by a method which includes the steps of:

(a) contacting a solid, pyridine ring-containing resin with an aqueous solution containing rhodium ion so that the rhodium ion is bound to the resin; and (b) contacting the rhodium ion-carrying resin with carbon monoxide and an alkyl iodide in an organic solvent so that the rhodium ion is converted to a rhodium complex bound to the resin. This method is also applicable to the production of conventional supported rhodium catalysts. Thus, any known VP resin can be also loaded with the rhodium complex using the above method.

In this method, the VP resin is first contacted with an aqueous solution containing rhodium ions so that the rhodium ions are bound to pyridine rings of the resin:

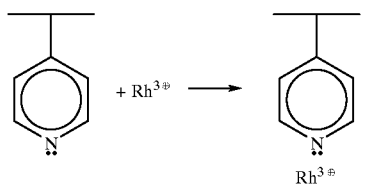

The aqueous solution may be prepared by dissolving a water soluble rhodium salt such as rhodium chloride, rhodium bromide or rhodium iodide and preferably has a rhodium concentration of 1,000–5,000 ppm by weight, more preferably 1,500–4,000 ppm by weight, in terms of elemental rhodium. The contact of the resin with the aqueous solution may be performed, for example, by immersing the resin in the solution or by passing the solution through a column packed with the resin at a temperature of generally 20–70° C., preferably 25–50° C., for a period of time so that desirably 0.2–2% by weight of rhodium ions in terms of elemental rhodium is bound to the resin.

The resin to which rhodium ions have been bound is then contacted with an alkyl iodide and carbon monoxide in an organic solvent so that the rhodium ion bound to the pyridine ring is converted into rhodium complex bound to the pyridinium nitrogen quaternized by reaction with the alkyl iodide:

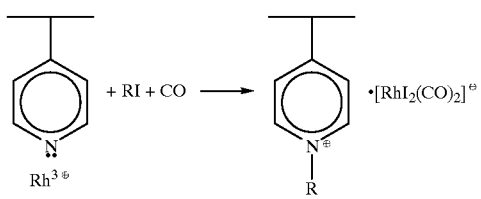

The alkyl iodide, which is preferably methyl iodide, is used in an amount of generally 2–2,000 moles, preferably 50–500 moles, per mole of the rhodium ions bound to the resin. As the organic solvent, there may be used alcohols such as methanol, ethanol and propanol, carboxylic acids such as acetic acid and propionic acid, esters such as methyl acetate, ethyl acetate and methyl propionate, and dialkyl ethers such as dimethyl ether. The organic solvent may contain up to 10% by weight of water. The amount of the rhodium ion-carrying resin is generally 2–25% by weight, preferably 5–10% by weight based on the weight of the organic solvent. The above reaction is generally performed at a temperature of 140–250° C., preferably 160–200° C. under a partial pressure of carbon monoxide of generally 5–30 kg/cm$^2$, preferably 10–25 kg/cm$^2$. The thus obtained rhodium complex loaded resin may be used as such for carbonylation of an alcohol but, if desired, may be separated from the reaction solvent and washed with an organic solvent such as methanol or acetic acid. The catalyst is placed in the reactor in an amount of generally 2–40% by weight based on the weight of the reaction solution contained therein.

Carbonylation Conditions:

As the reaction solvent, a carbonyl group-containing compound having at least two carbon atoms is suitably used. Such a compound may be, for example, a saturated aliphatic acid such as acetic acid, propionic acid or butyric acid, an ester such as methyl acetate or ethyl acetate, an aromatic acid such as benzoic acid, or a mixture thereof. The alkyl iodide is preferably a lower alkyl iodide having 1–6 carbon atoms, such as methyl iodide.

It is preferred that the content of the carbonyl group-containing solvent in the reactor be at least 0.16 mole, more preferably at least 1.28 moles, per mole of the carbonylatable compound. By using such an organic solvent in such a specific amount, the catalyst can exhibit high catalytic activity and the dissociation of rhodium species from the polymer substrate can be minimized, so that the reaction can be performed at a low carbon monoxide partial pressure. This is advantageous because it is not necessary to use a highly pressure-resisting reactor.

The carbonylation is performed at a temperature of 140–250° C., preferably 160–230°C. and a carbon monoxide partial pressure of 7–30 kg/cm$^2$, preferably 10–25 kg/cm$^2$. The alkyl iodide is used in an amount effective to promote the methanol carbonylation, generally in an amount of 1–40% by weight, preferably 5–30% by weight, based on the weight of the solution within the reactor. The rhodium loaded catalyst is used in a catalytically effective amount, generally in an amount of at least 50 ppm by weight, preferably at least 300 ppm by weight, more preferably at least 400 ppm by weight, in terms of elemental rhodium, based on the weight of the solution within the reactor.

In the conventional Monsanto method in which methanol is reacted with carbon monoxide in an acetic acid solution containing a rhodium compound and methyl iodide, water should be present in the catalyst solution in a large amount in order to accelerate the carbonylation and to improve selectivity. A high water content is also desired for the prevention of precipitation of the catalyst. Such a large amount of water causes the hydrolysis of the methyl iodide used as a reaction accelerator to form a large amount of hydrogen iodide which causes corrosion of apparatuses. Therefore, in the conventional homogeneous phase method, it has been essential to use a highly corrosion-resisting material, such as zirconium or Hastelloy B, which is very expensive, as the reactor.

The methanol carbonylation using methyl iodide as a co-catalyst involves the following side reactions (2) and (4) in addition to the main reaction (1):

$$CH_3OH + CO \rightleftharpoons CH_3COOH \quad (1)$$

$$CH_3COOH + CH_3OH \rightleftharpoons CH_3COOCH_3 + H_2O \quad (2)$$

$$2CH_3OH \rightleftharpoons CH_3OCH_3 + H_2O \quad (3)$$

$$CH_3I + H_2O \rightleftharpoons CH_3OH + HI \quad (4)$$

Thus, water is produced as a result of the side reactions (2) and (3). In the methanol carbonylation using the solid catalyst according to the present invention, a satisfactory carbonylation rate is obtainable even when the water concentration in the reaction solution is maintained at 10% by weight or less.

It has been found that when the water content in the reaction solution is maintained at 10% by weight or less, preferably 1–8% by weight, the interior surface of the reactor which is in contact with the reaction solution is prevented from being corroded, even when titanium which is much less expensive in comparison with zirconium or Hastelloy B is used for the material of the interior surface. On the other hand, that portion of the interior surface of the reactor which is not in contact with the reaction solution has been found to be exposed to corrosive conditions because of deposition of condensed liquid containing hydrogen iodide. Namely, the alkyl iodide contained in the condensed liquid reacts with hydrogen gas to form hydrogen iodide as follows:

$$H_2 + RI \rightarrow RH + HI$$

Therefore, when titanium is used as a material for the interior surface of the reactor which is exposed to the gas phase, the exposed portion is corroded.

It has now been found that a titanium/palladium alloy can withstand the chemical attack by hydrogen iodide. Thus, in one preferred embodiment, at least that surface of a carbonylation reactor which is brought into direct contact with a gas phase is formed of a titanium/palladium alloy which is much less expensive than zirconium or Hastelloy B. From the standpoint of economy, it is preferred those surfaces of the reactor which is brought into direct contact with a liquid phase be formed of titanium which is much less expensive than titanium/palladium alloy.

In the case of the contacting device shown in FIGS. 1 and 4, the interior surfaces of the device above and below the level H are formed of a titanium/palladium alloy and titanium, respectively. In the case of the contacting device shown in FIGS. 2 and 3, the interior surfaces of the device above and below the level H and H' are formed of a titanium/palladium alloy and titanium, respectively.

Figure 5:
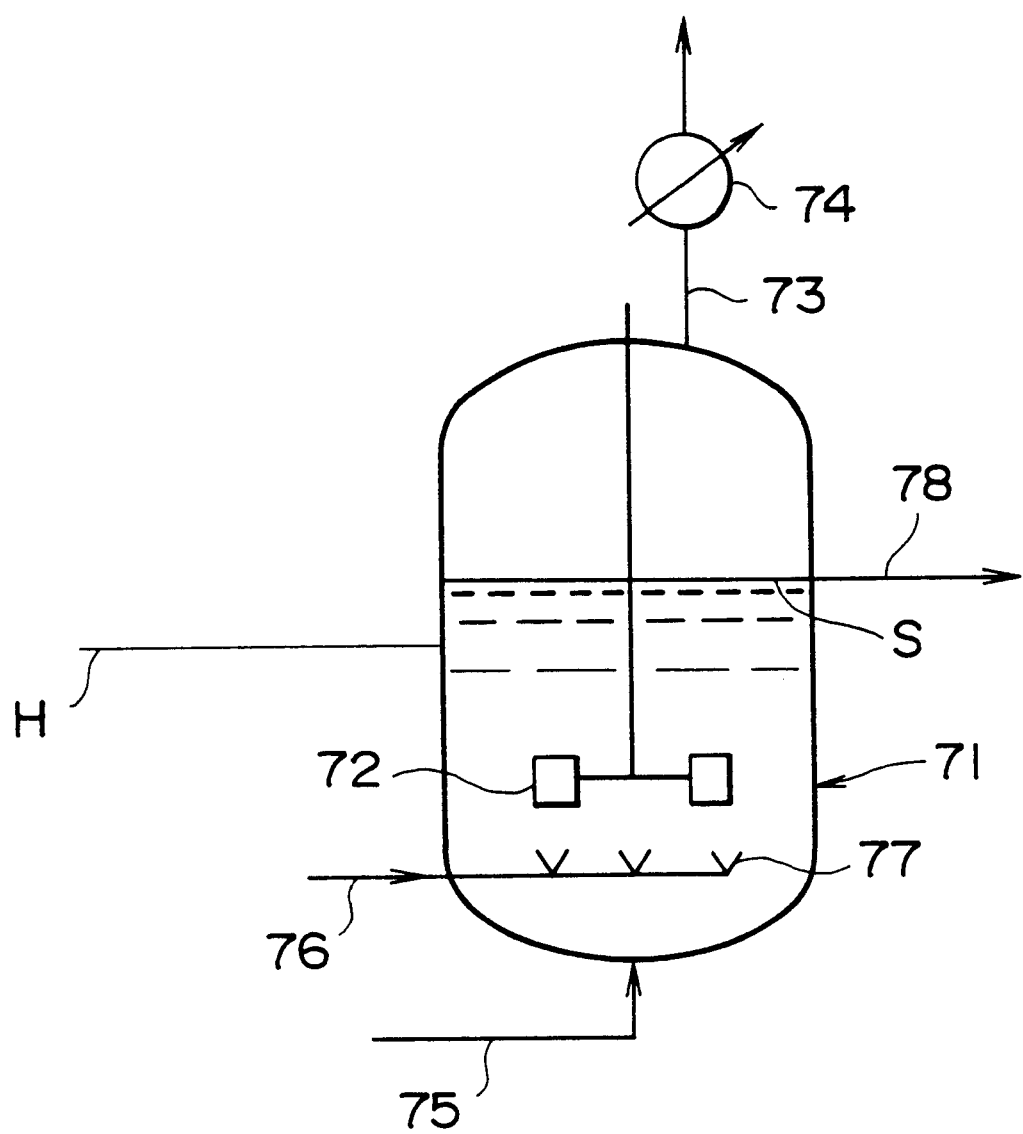

FIG. 5 illustrates a carbonylation reactor constructed to prevent the corrosion of the interior surface thereof. Designated as 71 is a reactor housing in which a mechanical stirrer 72 is disposed. The interior surfaces of the reactor housing 71 above and below the line H are formed of a titanium/palladium alloy and titanium, respectively. In performing the carbonylation, catalyst particles are placed in the reactor 71 and a mixed liquid containing a solvent, a raw material carbonylatable compound and an alkyl iodide is continuously fed through a line 75 into the reactor 71. The stirrer 72 is started to rotate and a carbon monoxide gas is injected into the mixture through a line 76 and nozzles 77. A part of the reaction solution is discharged through a line 78 and a gas phase containing unreacted carbon monoxide, by-product gases ($H_2$ and $CO_2$) and vapors of the solution is withdrawn overhead from the reactor 71 through a line 73. Condensable components in the gas phase is condensed in a condenser 74.

Titanium used for forming the foregoing reactors may be those specified in Japanese Industrial Standards JIS 1–3 Classes or a titanium-clad composite such as titanium-clad steel. The thickness of the titanium layer of the composite is generally at least 1 mm, preferably 2–10 mm, more preferably 3–10 mm. The titanium/palladium alloy generally has a palladium content of 0.05–50% by weight, preferably 0.1–0.3% by weight. Titanium/palladium alloys specified in Japanese Industrial Standards JIS 11–13 Classes or a titanium/palladium alloy-clad composite such as titanium/palladium alloy-clad steel. The thickness of the alloy layer of the composite is generally at least 1 mm, preferably 2–10 mm, more preferably 3–10 mm.

In construction, the reactor may be divided into a lower section having a titanium interior surface and an upper section having a titanium/palladium alloy surface. Each of the two sections may be provided with a flange so that the two sections may be connected to each other by bolting the flanges which are in abutting engagement with each other. Alternatively, when the two sections are formed of composites, the titanium layer and the alloy layer at end portions are first removed to expose the steel surface. Then, the two sections are abutted and welded together. A spacer is attached to a depressed portion defined by the removed portions. Thereafter, a titanium plate is applied onto the spacer and welded. The interconnected portion has been found to be free of problems of electric corrosion.

Corrosion of the interior surface which is exposed to the gas phase may be also achieved by washing the surface with a cleaning liquid containing less than 3,000 ppm by weight, preferably less than 1,500 ppm by weight, of hydrogen iodide. By this expedient, the entire interior surface of the contacting device can be made of titanium. The previously described titanium material may be used in this embodiment. Any liquid may be used as the washing liquid as long as it does not adversely affect the carbonylation and does not contain more than 3,000 ppm by weight of hydrogen iodide. Generally, an alcohol such as an aliphatic or aromatic alcohol, an ether such as a dialkyl ether, a carboxylic acid such as an aliphatic or aromatic carboxylic acid, or an ester such as an alkyl ester of an aliphatic or aromatic carboxylic acid is used. The raw material, the solvent or the reaction solution may be suitably used as the washing liquid.

It is preferred that the washing liquid be continuously applied to the interior surface of the reactor above the liquid level in an amount of 10–100 liter/hour, more preferably 50–100 liter/hour, per 1 $m^2$ of the interior surface. The washing may be suitably performed by continuously spraying the washing liquid toward the interior surface of the reactor form one or more spraying nozzles or spraying balls.

Figure 6:
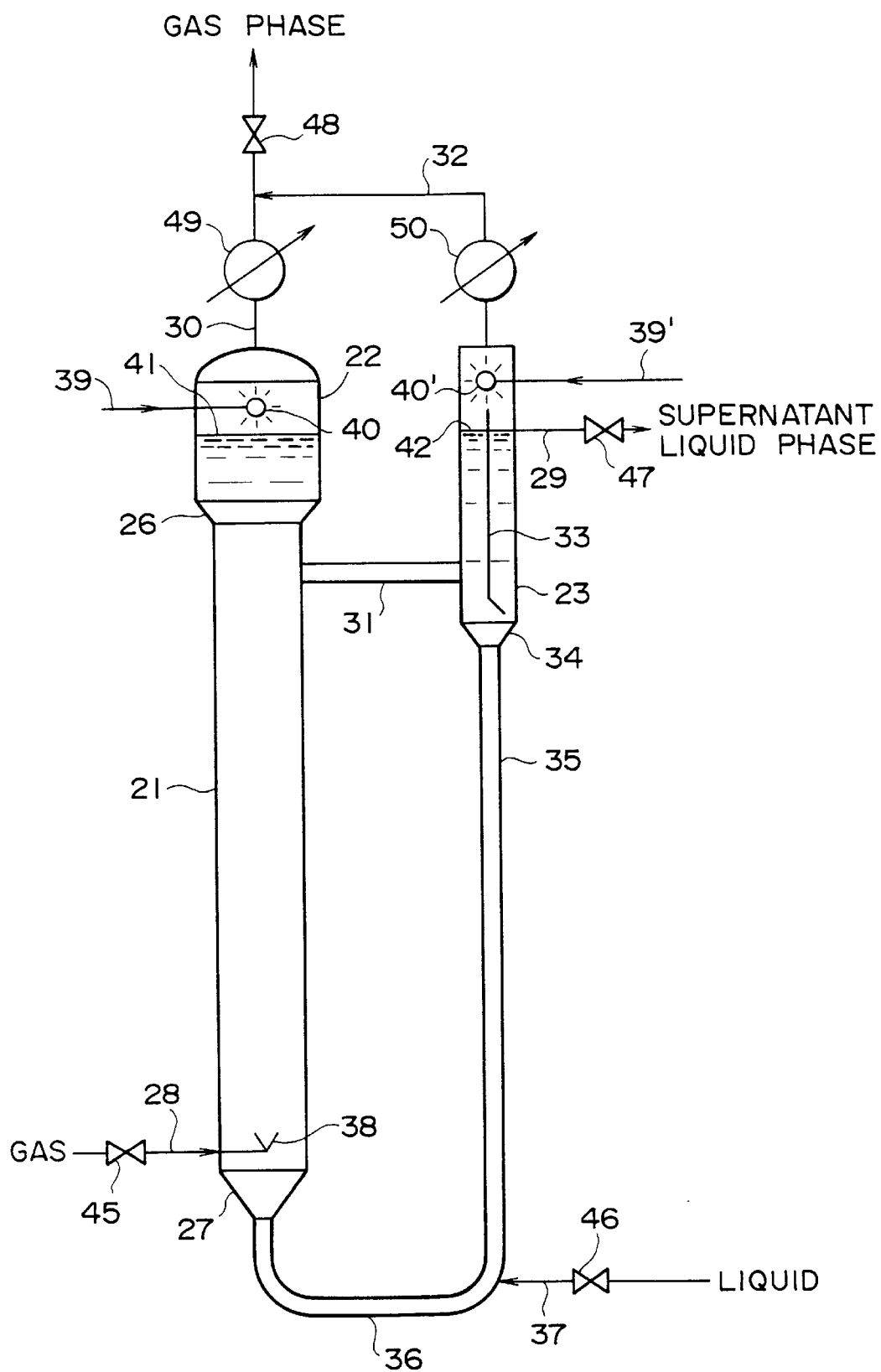

FIG. 6 illustrates an embodiment of the carbonylation reactor provided with the interior surface washing means.

The reactor is the same as shown in FIG. 3 except that the entire interior surface in this embodiment is formed of titanium and that washing liquid spraying means in the form of spraying balls 40 and 40' are disposed in the upper space above the liquid levels 41 and 42, respectively. The spraying means 40 and 40' are connected to washing liquid feed lines 39 and 39', respectively. It is without saying that similar spraying means can be incorporated into the contacting devices shown in FIGS. 1, 2, 4 and 5.

The following examples will further illustrate the present invention.

EXAMPLE 1
Hydrogenation of Benzene:

Into a reaction apparatus as shown in FIG. 1 were charged 90 g of Raney nickel powder catalyst. The reaction apparatus had a tubular vessel 1 having a height of 3,000 mm and an inside diameter of 20 mm, a gas separating chamber 2 having an inside diameter of 200 mm and a recycling pipe 3 having an inside diameter of 10 mm. Benzene (1,650 g) was then fed to the vessel 1 through a conduit 5 so that the liquid level was located 50 mm above the top end of the vessel 1. Hydrogen gas was then continuously fed through a conduit 4 to the vessel 1 at a rate of 1.7 normal liters per minute (NL/min), so that the mixture of the catalyst and benzene was recirculated through the vessel 1 and the pipe 3. In this case, valves 10–13 were controlled to maintain the pressure within the vessel 1 at about 30 kg/cm$^2$G and a temperature controlling device (heater) 9 was operated to maintain the temperature within the vessel 1 at 190° C. Then, benzene was continuously introduced through the conduit 5 into the vessel 1 at a rate of 3.8 g/min, while permitting a supernatant liquid to be discharged through a discharge conduit 7 and while maintaining the temperature within the vessel 1 at 190° C. After the feed rate of hydrogen gas had been increased to 3.4 NL/min, the hydrogenation was continued. The supernatant obtained in the steady state operation was analyzed to give the following results:

| Composition of Product | |
|---|---|
| Cyclohexane: | 3.84 g/min |
| Benzene: | 0.195 g/min |
| Others: | 0.02 g/min |
| Conversion of Benzene: | 94.9% |
| Selectivity to Cyclohexane: | 99.7% |

EXAMPLE 2
Carbonylation of Methanol:

Into a reaction apparatus similar to that used in Example 1 were charged 50 g of supported rhodium complex catalyst particles (specific gravity: 1.1, average particle diameter: 0.45 mm, vinylpyridine resin particles carrying rhodium complex). Acetic acid (1,650 g) was then fed to the vessel 1 through the conduit 5 so that the liquid level was located 50 mm above the top end of the vessel 1. Carbon monoxide gas was then continuously fed through the conduit 4 to the vessel 1 at a rate of 5.0 NL/min, so that the mixture of the catalyst and acetic acid was recirculated through the vessel 1 and the pipe 3. In this case, valves 10–13 were controlled to maintain the pressure within the vessel 1 at about 45 kg/cm$^2$G and the heater 9 was operated to maintain the temperature within the vessel 1 at 180°C. Then, a raw material feed having the composition shown below was continuously introduced through the conduit 5 into the vessel 1 at a rate of 22.2 g/min, while permitting a supernatant liquid to be discharged through a discharge conduit 7 and while maintaining the temperature within the vessel 1 at 180°C. After the feed rate of hydrogen gas had been increased to 11.3 NL/min, the carbonylation was continued. The supernatant obtained in the steady state operation was analyzed to give the following results:

| Composition of Raw Material: | |
|---|---|
| Methanol: | 5.0 g/min |
| Methyl iodide: | 2.2 g/min |
| Acetic acid: | 13.0 g/min |
| Composition of Product: | |
| Acetic acid: | 13.7 g/min |
| Methanol: | 0.12 g/min |
| Methyl acetate: | 5.1 g/min |
| Methyl iodide: | 2.2 g/min |
| Water: | 1.2 g/min |
| Others:. | 0.01 g/min |
| Conversion of Methanol: | 98% |
| Selectivity to Acetic Acid: | >99% |

EXAMPLE 3
Hyroformylation of Propylene:

Chloromethylated styrene/divinyl benzene resin particles (50 g, Bio-Rad, SX-1) were swelled with 400 ml tetrahydrofuran, to which 200 ml of a tetrahydrofuran solution containing 0.23 moles of LiPPh were added dropwise. The mixture was then gently stirred for 24 hours. After being diluted with about 1 liter of toluene, the reaction mixture was filtered and the solids were dried under vacuum to obtain 54 g of resin particles. The resulting resin was mixed with 2 g of RhCl(PPh$_3$)$_2$ in 500 ml of toluene and the mixture was reacted in a nitrogen stream for 3 days. The mixture was then filtered and the solids were sufficiently washed with toluene to obtain hydroformylation catalyst particles.

The above particles were used for hydroformylation of propylene using a reaction apparatus similar to that used in Example 1. Thus, toluene was fed to the vessel through the conduit 5 until the liquid level was located 50 mm at the top end of the vessel 1. Then the above catalyst particles were introduced into the separating chamber 2 from a top end thereof, while feeding nitrogen gas through the conduit 4 to the vessel 1. After purging with 5 kg/cm$^2$ of nitrogen gas, 4.7 NL/min of a mixed gas of CO/H$_2$ (1/1 mol/mol) were fed through the conduit 4 to the vessel 1 to recirculate the mixture in the vessel 1 through the vessel 1 and the pipe 3 and to heat the mixture to 120° C. with the heater 9. Then, propylene gas was fed to the vessel 1 at a rate of 1.6 NL/min through the conduit 4 together with 3.1 NL/hour of the mixed CO/H$_2$ gas, while feeding toluene through the conduit 5 at a rate of 1 liter per hour and while permitting a supernatant liquid to be discharged through a discharge conduit 7. In this case, the valve 11 was controlled to maintain the pressure within the vessel 1 at about 5 kg/cm$^2$G. The supernatant obtained 10 hours after the commencement of the propylene feed was analyzed by gas chromatography to reveal that the n-butylaldehyde content and iso-butylaldehyde content were 0.12% by weight and 0.08% by weight, respectively.

REFERENCE EXAMPLE 1
Carbonylation of Methanol at Low Moisture Concentration Using Homogeneous Catalyst:

Into a 250 ml autoclave having an interior surface of titanium were charged 14 g of methanol, 14 g of methyl iodide, 112 g of acetic acid and 0.14 g of RhCl$_3$.H$_2$O. After purging twice with 50 kg/cm$^2$ nitrogen gas, the mixture in the autoclave was heated to 180° C. with stirring at 1400 rpm. In this case, carbon monoxide gas was fed to the autoclave through an automatic pressure control valve so that the total pressure within the autoclave was 50 kg/cm$^2$G when the autoclave temperature of 180° was reached. The control valve was connected to a 0.6 liter reservoir tank having an initial carbon monoxide pressure of 70 kg/cm$^2$. A decreasing rate of the carbon monoxide pressure in the reservoir tank represents the rate of reaction of carbon monoxide. The reaction was continued for 35 minutes from the commencement of the carbon monoxide feed. The reaction rate per unit volume of the reaction mixture was found to be 1.3 mol/liter/hour, whereas the reaction rate per mole of Rh was found to be 320 mol/Rh(mol)/hour. The autoclave was then quickly cooled. After purging twice with 50 kg/cm$^2$ nitrogen, the reaction mixture was recovered and analyzed by gas chromatography for the concentrations of methanol, methyl iodide, water, acetic acid, methyl acetate and dimethyl ether and by potentiometric titration for the concentration of hydrogen iodide. The results are summarized in Table 1 together with the reaction conditions and the composition of the raw materials.

REFERENCE EXAMPLE 2

Carbonylation of Methanol at Low Moisture Concentration Using Heterogeneous Catalyst:

A supported rhodium catalyst was prepared as follows:

A 4-vinylpyridine-divinylbenzene resin (cross-linking degree: 59%; 6.7 g (on dry basis)) was swelled well with methanol and charged in a 250 ml autoclave, having an interior surface of titanium and equipped with a stirring blade, together with 140 g of a solution consisting of 45% by weight of methanol, 47% by weight of acetic acid and 8% by weight of methyl iodide and 0.14 g of RhCl$_3$. H$_2$O. After deaeration several times with 50 kg/cm$^2$G nitrogen, the autoclave was heated to 190° C. Then, carbon monoxide was charged into the autoclave through an automatic pressure control valve until a total pressure of 50 kg/cm$^2$ resulted (initial carbon monoxide partial pressure: 150 kg/cm$^2$). After 30 minutes reaction, the autoclave was cooled and purged with nitrogen gas. The supernatant was removed by decantation and the solids were washed several times with methanol to obtain a rhodium-loaded resin catalyst. The atomic absorption analysis and gas chromatography of the supernatant revealed that the catalyst had a Rh content of 0.8% based on the weight of the resin and an iodine content of about 1 equivalent per one pyridine ring.

Reference Example 1 was then repeated in the same manner as described except that the thus obtained rhodium-loaded resin catalyst (10 g (dry weight)) was used in place of the RhCl$_3$.H$_2$O catalyst and that the mixed liquid used consisted of 98 g of acetic acid, 28 g of methanol and 14 g of methyl iodide. The reaction rate per unit volume of the reaction mixture was found to be 4.3 mol/liter/hour, whereas the reaction rate per mole of Rh was found to be 1,070 mol/Rh(mol)/hour. The reaction product had a composition as summarized in Table 1.

REFERENCE EXAMPLE 3

Carbonylation of Methanol at High Moisture Concentration Using Homogeneous Catalyst:

Reference Example 1 was repeated in the same manner as described except that 14 g of methanol, 14 g of methyl iodide, 21 g of water, 91 g of acetic acid and 0.14 g of RhCl$_3$. H$_2$O were reacted. The reaction rate per unit volume of the reaction mixture was found to be 4.4 mol/liter/hour, whereas the reaction rate per mole of Rh was found to be 1,090 mol/Rh(mol)/hour. The reaction product had a composition as summarized in Table 1.

TABLE 1

| Reference Example No. | 1 | 2 | 3 |
|---|---|---|---|
| Temperature (° C.) | 180 | 180 | 180 |
| Pressure (kg/cm$^2$) | 50 | 50 | 50 |
| Raw Material Composition | | | |
| Methanol (wt %) | 10 | 20 | 10 |
| Methyl iodide (wt %) | 10 | 10 | 10 |
| Water (wt %) | 0 | 0 | 10 |
| Acetic acid (wt %) | 80 | 70 | 65 |
| RhCl$_3$ · 3H$_2$O (wt ppm) | 400 | 400* | 400 |
| Amount (g) | 140 | 140 | 140 |
| Reaction Mixture | | | |
| Methanol (wt %) | 0.3 | 0.6 | 0.1 |
| Methyl iodide (wt %) | 7.8 | 7.2 | 6.1 |
| Water (wt %) | 3.8 | 4.8 | 13.6 |
| Acetic acid (wt %) | 72.6 | 66.1 | 97.7 |
| Methyl acetate (wt %) | 15.5 | 21.3 | 2.4 |
| Dimethyl ether (wt %) | 0.1 | 0.1 | 0.1 |
| Hydrogen iodide (wt ppm) | 110 | 400 | 15,100 |
| Reaction Rate (mol/liter/hr) | 1.3 | 4.3 | 4.4 |

*as supported catalyst

REFERENCE EXAMPLES 4–7

Relationship between Hydrogen Iodide Concentration and Corrosion of Titanium in Contact with Reaction Mixture:

In an autoclave whose interior surface was coated with a tetrafluoroethylene resin was disposed a stirrer having a stirring blade and a rotating shaft both coated with the same resin. The autoclave was provided with a liquid raw material feed port and a carbon monoxide feed port in a lower part thereof and with a liquid discharge port at such a position that the inside volume of the autoclave below the discharge port was 120 ml. A test piece made of titanium (according to JIS H4600) was disposed in the autoclave at a position below the discharge port. A catalyst prepared in the same manner as described in Reference Example 2 was placed in the autoclave, to which a liquid raw material and carbon monoxide gas were continuously fed. The liquid raw material used in Reference Example 4 consisted of acetic acid, methanol and methyl iodide, while that used in Reference Examples 5–7 further contained water. The amount of the carbon monoxide gas feed was 1.2 times the stoichiometric amount. An automatic pressure control valve was connected to a top of the autoclave to keep the pressure within the autoclave constant. The reaction was continued for 100 hours. The reaction conditions and the results were as summarized in Table 2.

TABLE 2

| Reference Example No. | 4 | 5 | 6 | 7 |
|---|---|---|---|---|
| Temperature (° C.) | 180 | 180 | 180 | 180 |
| Pressure (kg/cm$^2$) | 50 | 50 | 50 | 50 |
| Residence Time (hour) | 1 | 1 | 1 | 1 |
| Reaction Mixture | | | | |
| Dimethyl ether (wt %) | 0.0 | 0.0 | 0.0 | 0.0 |
| Water (wt %) | 6.1 | 9.8 | 13.3 | 14.3 |
| Methanol (wt %) | 0.0 | 0.0 | 0.0 | 0.0 |
| Methyl iodide (wt %) | 6.5 | 5.3 | 5.1 | 4.4 |
| Methyl acetate (wt %) | 1.7 | 0.5 | 0.1 | 0.2 |
| Acetic acid (wt %) | 85.6 | 84.1 | 81.4 | 77.9 |
| Hydrogen iodide (wt ppm) | 300 | 2900 | 8700 | 32100 |
| Appearance of Test Piece | metallic luster | metallic luster | local corrosion | local corrosion |

From the results shown in Table 2, it will be seen that the amount of hydrogen iodide, produced by hydrolysis of methyl iodide, exponentially increases with an increase in water concentration in the reaction mixture and that titanium which is in contact with a liquid phase having a hydrogen iodide concentration of not greater than 3,000 ppm (namely, when the water concentration in the reaction mixture is not greater than 10% by weight) does not corrode.

REFERENCE EXAMPLES 8–11

Corrosion of Titanium in Gas Phase above Reaction Mixture:

In a 300 ml glass autoclave, 150 ml of a mixture of methanol, water, acetic acid and hydrogen iodide having a composition shown in Table 3 was charged. A titanium test piece was then placed in the space above the mixture in the autoclave. After purging five times with 10 kg/cm$^2$ nitrogen gas, the mixture was boiled at 140° C. for 5 minutes to remove oxygen contained therein. The mixture was cooled to room temperature and was purged with 10 kg/cm$^2$ carbon monoxide gas. Then, the mixture was heated to 180° C. and held at that temperature for 96 hours while maintaining the pressure within the autoclave at 9 kg/cm$^2$ by introducing carbon monoxide gas and, in the case of Reference Examples 8, 10 and 11, hydrogen gas. It was found that the test piece was kept wetted with a condensed liquid throughout the above corrosion test. Subsequently, the autoclave was cooled to room temperature and purged well with nitrogen. The test piece was taken out of the autoclave and measured for the corrosion rate in terms of the weight loss. A sample whose weight loss is less than 0.01 mg/year is regarded as being uncorroded. The reaction mixture, on the other hand, was measured for the concentration of hydrogen iodide by potentiometric titration. The results are summarized in Table 3.

TABLE 3

| Reference Example No. | 8 | 9 | 10 | 11 |
|---|---|---|---|---|
| Test Time (hour) | 96 | 96 | 96 | 96 |
| Temperature (° C.) | 180 | 180 | 180 | 180 |
| Total Pressure (kg/cm$^2$) | 9 | 9 | 9 | 9 |
| Carbon Monoxide Partial Pressure (kg/cm2) | 2.5 | 2.3 | 1.5 | 1.5 |
| Hydrogen Partial Pressure (kg/cm2) | 1.5 | 0 | 1.5 | 0.1 |
| Test Liquid | | | | |
| Water (wt %) | 5 | 5 | 5 | 5 |
| Methyl iodide (wt %) | 0 | 3 | 3 | 3 |
| Acetic acid (wt %) | 95 | 92 | 92 | 92 |
| Hydrogen iodide (wt ppm) | 1470 | 1830 | 1370 | 2410 |
| Corrosion Rate (mg/year) | none | none | 0.2 | 0.05 |

REFERENCE EXAMPLE 12 corrosion of Titanium in Dried State:

A titanium test piece was disposed in a tubular glass reactor having a length of 30 cm and an inside diameter of 20 mm. The reactor was placed in an electric oven and heated to 180° C. while streaming a nitrogen gas from the top of the reactor. Then, a hydrogen gas was fed from an upper portion of the reactor at a rate of 3.4 ml/min together with 0.5 ml/hour of a mixed liquid consisting of 14.5% by weight of methanol, 18.8% by weight of acetic acid, 23.4% by weight of methyl acetate, 43.0% by weight of methyl iodide, 0.3% by weight of water and 0.5% by weight of hydrogen iodide. The mixed liquid was found to be completely vaporized in a moment as soon as it entered the reactor, so that the test piece was always maintained in a dried state. No corrosion was found in the test piece after the 170 hours test.

The results obtained in Reference Examples 8–12 suggest that corrosion of the titanium test piece in the gas phase occurs when the liquid phase contains methyl iodide, when the gas phase contains hydrogen and when the test piece is wetted with a condensate.

EXAMPLE 4

Reference Example 10 was repeated in the same manner as described except that a titanium/palladium alloy test piece was substituted for the titanium test piece. No corrosion of the test piece was observed.

EXAMPLE 5

Reference Example 4 was repeated in the same manner as described except that the reaction conditions, the liquid raw material, the gas feed, the autoclave and the stirrer used were changed as follows. The interior surface of the autoclave was formed of a titanium/palladium alloy, the stirrer was composed of a titanium/palladium alloy shaft to which a titanium shaft was welded, and a stirring blade formed of a titanium/palladium alloy was fixed to the titanium shaft with screws. The liquid raw material consisted of 17% by weight of methyl iodide, 32% by weight of methanol and 51% by weight of acetic acid. The gas feed consisted of a mixture of 95 parts by volume of carbon monoxide and 5 parts by volume of hydrogen. The reaction conditions involved a temperature of 180° C., a pressure of 40 kg/cm$^2$G and a residence time of 2 hours.

The reaction was continued for 1,000 hours. The amount of the gas feed was 1.2 times the stoichiometric amount. An automatic pressure control valve was connected to a top of the autoclave to keep the pressure within the autoclave constant. No catalyst deactivation was observed and the reaction mixture had substantially the same composition throughout the 1,000 hours process time as follows: 13.6% by weight of methyl iodide, 0.1% by weight of methyl ketone, 0.6% by weight of methanol, 21.7% by weight of methyl acetate, 58.2% by weight of acetic acid and 5.8% by weight of water. No corrosion of the interior surface (both above and below the liquid discharge port) of the autoclave was observed. No corrosion of the stirrer shaft and blade was observed. The X-ray spectrophotoelectric analysis revealed that a titanium oxide film was formed on the titanium surface and the titanium/palladium alloy surface.

EXAMPLE 6

Reference Example 10 was repeated in the same manner as described except that a portion of the reaction mixture was continuously discharged from the autoclave and sprayed over the surface of the titanium test piece. No corrosion of the test piece was observed after the 96 hours test.

EXAMPLE 7

Reference Example 4 was repeated in the same manner as described except that an autoclave having an interior surface formed of titanium was replaced for the resin-coated autoclave and that a portion of the reaction mixture discharged from the liquid discharge port was sprayed over the interior surface of the autoclave which was in contact with the gas phase above the liquid level. No corrosion of the interior surface (both above and below the liquid discharge port) of the autoclave was observed after the 1,000 hours test. The hydrogen content in the titanium test piece after the test was found to remain unchanged. The X-ray spectrophotoelectric analysis revealed that a titanium oxide film was formed on the surface of the test piece.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A device for contacting catalyst particles with gas and liquid phases, said device comprising:
    (a) a vertically extending cylindrical vessel having upper and lower portions;
    (b) catalyst particles and a liquid, said liquid having a specific gravity smaller than that of the catalyst particles, said liquid, with the catalyst particles dispersed therein, filling said cylindrical vessel;
    (c) a liquid feed conduit connected to said lower portion for feeding said liquid to said vessel;
    (d) gas injection means provided in said lower portion for injecting said gas into said vessel and for bubbling said gas through said liquid such that an upwardly flowing mixture comprising said liquid, said particles and said gas is formed within said vessel;
    (e) a gas separating chamber disposed adjacent to said upper portion of said vessel for receiving said upwardly flowing mixture and separating said upwardly flowing mixture by gravity into a gas phase, a supernatant liquid phase and a phase rich in said catalyst particles, said upwardly flowing mixture partially filling said gas separating chamber to define a normal liquid level therein;
    (f) a gas discharge conduit connected to a top portion of said separating chamber, above said normal liquid level, for withdrawing said gas phase from said separating chamber;
    (g) a liquid discharge conduit connected to an upper portion of said separating chamber, below said normal liquid level, for discharging a portion of said supernatant liquid phase from said separating chamber; and
    (h) a recycling path extending between said separating chamber and said lower portion of said vessel for recycling said catalyst particles-rich phase from said separating chamber to said vessel by gravity.

2. A device as set forth in claim 1, further comprising temperature controlling means provided in said recycling path for controlling the temperature of said catalyst particles-rich phase to be recycled to said vessel.

3. A device as set forth in claim 1, wherein that surface of said separating chamber which is brought into direct contact with said gas phase is formed of a titanium/palladium alloy, while those surfaces of said vessel and separating chamber which are brought into direct contact with at least one of said liquid, supernatant phase and catalyst particles-rich phase are formed of titanium.

4. A device as set forth in claim 1, wherein the surfaces of said vessel and said separating chamber are formed of titanium.

5. A device as set forth in claim 4, further comprising means disposed in said separating chamber for applying a cleaning liquid to that surface of said separating chamber which is brought into direct contact with said gas phase.

6. A device as set forth in claim 1 wherein said liquid discharge conduit connects to said upper portion of said gas separating chamber at a liquid discharge port in a side wall of said gas separating chamber, and further comprising a plate vertically disposed in said gas separating chamber between said liquid discharge port and an upper end of said vessel terminating within said gas separating chamber, said plate vertically extending between a point below said normal liquid level and a point above said normal liquid level to prevent liquid exiting said upper end and containing gas entrained therein from directly entering said liquid discharge conduit.

7. A device for contacting catalyst particles with gas and liquid phases, said device comprising:
    (a) a vertically extending cylindrical vessel having upper and lower portions;
    (b) catalyst particles and a liquid, said liquid having a specific gravity smaller than that of the catalyst particles, said liquid, with the catalyst particles dispersed therein, filling said cylindrical vessel;
    (c) a liquid feed conduit connected to said lower portion for feeding said liquid to said vessel therethrough;
    (d) gas injection means provided in said lower portion for injecting said gas into said vessel and for bubbling said gas through said liquid such that an upwardly flowing mixture of said liquid, said gas and said catalyst particles is formed within said vessel;
    (e) a first separating chamber connected to said upper portion of said vessel for receiving said upwardly flowing mixture and separating said upwardly flowing mixture by gravity into a first gas phase, a first supernatant liquid phase and a first catalyst particles-rich phase, said upwardly flowing mixture partially filling said first gas separating chamber to define a first normal liquid level therein;
    (f) a gas discharge conduit connected to a top portion of said first separating chamber, above said first normal liquid level, for withdrawing said first gas phase from said first separating chamber;
    (g) a second separating chamber connected to said upper portion of said vessel, so that a portion of said upwardly flowing mixture and a portion of said first catalyst particles-rich phase are introduced into said second separating chamber, to partially fill and establish a second normal liquid level in said second separating chamber, and are separated into a second gas phase, a second supernatant liquid phase and a second catalyst particle-rich phase;
    (h) a gas withdrawing conduit connected to a top portion of said second separating chamber, above said second normal liquid level, for discharging said second gas phase from said second separating chamber;
    (i) a liquid discharge conduit connected to an upper portion of one of said first and second separating chambers, below one of said first and second normal liquid levels, for discharging a portion of said first or second supernatant liquid phase from said first or second separating chambers; and
    (j) a recycling path extending between said degassing chamber and said lower portion of said vessel for recycling said catalyst particle-containing liquid from said degassing chamber to said vessel by gravity.

8. A device as set forth in claim 7, further comprising temperature controlling means provided in said recycling path for controlling the temperature of said second catalyst particles-rich phase to be recycled to said vessel.

9. A device as set forth in claim 7, wherein those surfaces of said first and second separating chambers which are brought into direct contact with said first and second gas phases, respectively, are formed of a titanium/palladium alloy, while those surfaces of said vessel and said first and second separating chambers which are brought into direct contact with at least one of said liquid, said first and second supernatant liquid phases and said first and second catalyst particles-rich phases are formed of titanium.

10. A device as set forth in claim 7, wherein the surfaces of said vessel and said first and second separating chambers are formed of titanium.

11. A device as set forth in claim 10, further comprising means disposed in each of said first and second separating chambers for applying a cleaning liquid to those surfaces of said first and second separating chambers which are brought into direct contact with said first and second gas phases, respectively.

12. A device as set forth in claim 7, wherein each of said first and second separating chambers has a horizontal sectional area greater than that of said vessel.

13. A device as set forth in claim 7 wherein said liquid discharge conduit connects a liquid discharge port formed in a side wall of said second separating chamber with a port located in said upper portion of said cylindrical vessel and located below said first separating chamber.

* * * * *